United States Patent [19]
Shirk et al.

[11] Patent Number: 5,979,934
[45] Date of Patent: Nov. 9, 1999

[54] DEVICE FOR DETECTING A DECREASE IN HYDROGEN PRESSURE IN AN AIR-BAG INFLATION SYSTEM

[75] Inventors: Bryan W. Shirk; Timothy A. Swann, both of Mesa; Ahmad K. Al-Amin, Higley, all of Ariz.

[73] Assignee: TRW Inc., Lyndhurst, Ohio

[21] Appl. No.: 08/969,024

[22] Filed: Nov. 12, 1997

[51] Int. Cl.[6] .............................. B62K 1/00; B60Q 1/00
[52] U.S. Cl. .................... 280/735; 280/741; 340/436; 340/438
[58] Field of Search .................... 73/23.2, 31.03, 73/31.02, 31.06; 280/728.1, 741, 736, 735, 743.1; 180/268, 281, 282, 286, 289, 265; 340/436, 438

[56] References Cited

U.S. PATENT DOCUMENTS

| | | | |
|---|---|---|---|
| 5,263,740 | 11/1993 | Frey et al. ............................. | 280/737 |
| 5,351,527 | 10/1994 | Blackburn et al. . | |
| 5,375,456 | 12/1994 | Burns . | |
| 5,428,988 | 7/1995 | Starkovich . | |
| 5,466,313 | 11/1995 | Brede et al. ............................. | 149/1 |
| 5,520,753 | 5/1996 | Hunter ............................. | 148/430 |
| 5,551,723 | 9/1996 | Mahon et al. ............................. | 280/737 |
| 5,591,900 | 1/1997 | Bronowocki et al. . | |
| 5,668,301 | 9/1997 | Hunter ............................. | 73/23.2 |

OTHER PUBLICATIONS

Article entitled "Automated Hydrogen Gas Leak Detection System" (NASA Lewis Research), Apr. 16, 1996.
Article entitled "Chemical Species Gas Sensors Team Home Page", (NASA Lewis Research).

*Primary Examiner*—Hezron Williams
*Assistant Examiner*—Jay L.. Politzer
*Attorney, Agent, or Firm*—Tarolli, Sundheim, Covell, Tummino & Szabo

[57] ABSTRACT

An apparatus (2) comprises an inflatable vehicle occupant restraint (4) for, when inflated, helping to protect a vehicle occupant. An inflator (10) is provided having a housing (12) defining a chamber (30). A mixture of gases (32) is stored in the chamber for inflating the vehicle occupant restraint (4). A diode (60) is supported by the housing (12) and is exposed to the stored mixture of gases (32) in the chamber (30). An electrical property of the diode (60) is dependent upon the concentration of at least one of the gases in the mixture of gases (32) in the chamber (30). In a preferred embodiment, sensor means (70) is provided for sensing the electrical property of the diode (60). The sensor means (70) provides an output signal when the electrical property of the diode reaches a predetermined threshold indicating a reduction in the concentration of the one gas in the mixture of gases (32). Means responsive to the output signal (74) is provided for affecting vehicle occupant safety.

9 Claims, 2 Drawing Sheets

DEVICE FOR DETECTING A DECREASE IN HYDROGEN PRESSURE IN AIR-BAG INFLATION SYSTEM

TECHNICAL FIELD

The present invention relates to an inflatable vehicle occupant restraint system, and particularly to an inflator for storing gas to inflate an inflatable vehicle occupant restraint and having a sensor for detecting leakage of gas from the inflator.

BACKGROUND OF THE INVENTION

A known inflator stores gas for inflating an inflatable vehicle occupant restraint, such as an air bag. The gas typically comprises a mixture of at least two different gases. The gas is directed into the air bag to inflate the air bag to help protect the vehicle occupant from a forceful impact with parts of the vehicle on sudden vehicle deceleration. It is desirable to be able to detect gas leakage from the inflator over the life of the inflator, since a reduction in the amount of gas stored in the inflator could affect inflation of the air bag.

SUMMARY OF THE INVENTION

The present invention relates to an apparatus comprising an inflatable vehicle occupant restraint for, when inflated, helping to protect a vehicle occupant in the event of a vehicle collision. An inflator for the inflatable vehicle occupant restraint has a housing defining a chamber. A mixture of gases for inflating the vehicle occupant restraint is stored in the chamber. A diode is supported by the housing and is exposed to the stored mixture of gases in the chamber. An electrical property of the diode is dependent upon the concentration of at least one of the gases in the mixture of gases in the chamber.

Further, in accordance with the present invention, sensor means senses the electrical property of the diode. The sensor means provides an output signal when the electrical property of the diode reaches a predetermined threshold indicating a reduction in the concentration of the at least one of the gases in the mixture of gases. Means responsive to the output signal, such as a warning indicator, is provided for the vehicle occupant's safety.

BRIEF DESCRIPTION OF THE DRAWINGS

The foregoing and other features of the invention will become more apparent to one skilled in the art upon consideration of the following description of the invention and the accompanying drawings in which.

DESCRIPTION OF PREFERRED EMBODIMENTS

Figure 1:
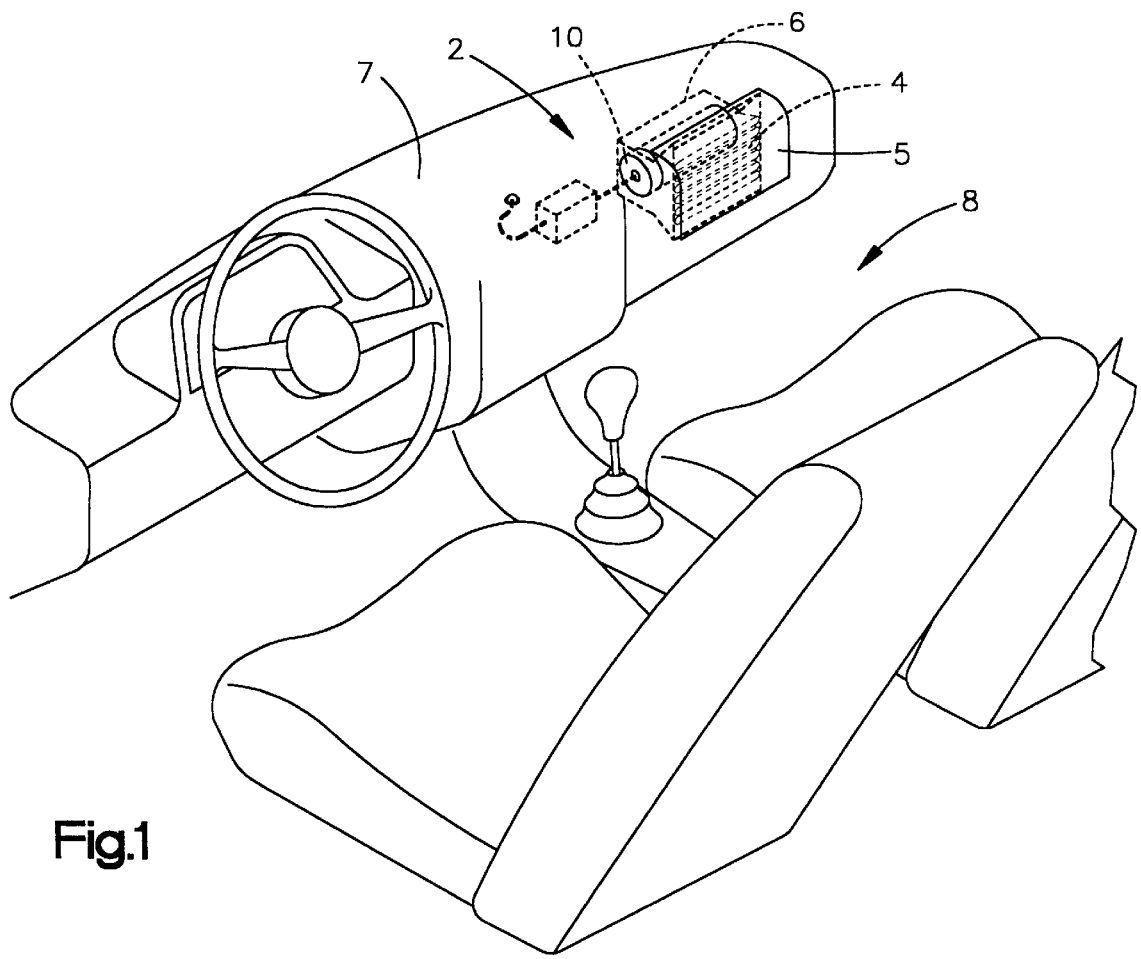
FIG. 1 is a schematic view of a vehicle occupant protection system which is constructed in accordance with a first embodiment of the present invention.

Referring to FIG. 1, a vehicle occupant protection system 2 includes an inflatable vehicle occupant protection device 4. In the preferred embodiment of the present invention, the protection device 4 is an air bag shown schematically in its folded and deflated condition. Other inflatable vehicle occupant protection devices with which the present invention could be used include inflatable seat belts, inflatable knee bolsters, inflatable head liners or side curtains, and knee bolsters operated by inflatable air bags.

An inflator 10 is associated with the inflatable vehicle occupant protection device 4. The inflator 10 is actuatable to direct inflation fluid for inflating the air bag 4 into the air bag.

The inflator 10 and the air bag 4 are housed in a reaction canister 6. The reaction canister 6 is disposed behind an air bag deployment door 5 in an instrument panel 7 of an occupant compartment 8 of a vehicle.

The system 2 also includes a crash sensor (not illustrated). The crash sensor is a known device that senses a vehicle condition, such as vehicle deceleration, indicative of a collision. The crash sensor measures the magnitude and duration of the deceleration. If the magnitude and duration of the deceleration meet or exceed predetermined threshold levels, a deployment signal is then transmitted to the inflator 10 to actuate the inflator.

Figure 2:
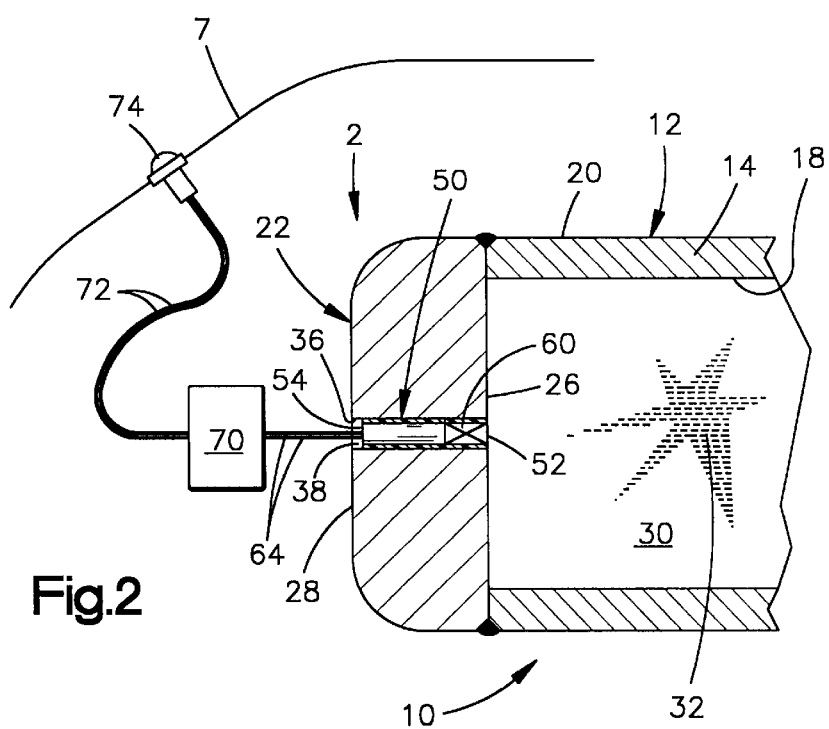
FIG. 2 is a schematic view, partly in section, of a portion of the vehicle occupant protection system of FIG. 1.

In the preferred embodiment of the invention, the inflator 10 (FIG. 2) includes a generally cylindrical container 12 made of a suitable material such as steel or aluminum. The container 12 includes a generally cylindrical wall 14. The wall 14 includes a cylindrical inner surface 18 having a first diameter. The wall 14 further includes a cylindrical outer surface 20 having a second diameter, larger than the first diameter.

The container 12 includes a schematically shown first end wall or end cap 22 at one end of the wall 14 and a second end wall or end cap (not shown) at the opposite end of the wall. The first end cap 22 includes a first circular wall surface 26 and a second circular wall surface 28 spaced a distance from the first circular wall surface.

The wall 14, the first end cap 22 and the second end cap define a chamber 30 in the container 12 which holds a supply of gas 32 for inflating the air bag 4. Specifically, the chamber 30 is defined in part by the cylindrical inner surface 18 of the wall 14 and the first circular wall surface 26 of the first end cap 22.

The air bag inflation gas 32 in the preferred embodiment of the invention comprises a mixture of gases including an inert gas, a combustible fuel gas and an oxidizer gas. The inert gas is preferably nitrogen, argon or a mixture of nitrogen and argon. The fuel gas is preferably hydrogen or a mixture of hydrogen and a hydrocarbon, such as methane. The oxidizer gas is preferably oxygen. In another specific embodiment, the air bag inflation gas 32 comprises air and hydrogen.

The air bag inflation gas 32 within the container 12 is normally under pressure. The pressure depends upon such factors as the volume of the air bag 4 to be inflated, the time available for inflation, the inflation pressure desired, the volume of the container 12 storing the air bag inflation gas 32, and the molar percentage of each of the gases in the air bag inflation gas. The air bag inflation gas 32 in the chamber 30 is typically at a pressure of about 500 to about 5,000 pounds per square inch (psi). Preferably, the air bag inflation gas 32 in the chamber 30 is at a pressure of about 2,000 to about 4,000 psi.

Upon the occurrence of vehicle deceleration indicative of a collision for which inflation of the air bag 4 is desired, the sensor activates an igniter (not shown) to ignite the fuel gas in the air bag inflation gas 32. The oxidizer gas supports the combustion of the fuel gas.

Burning of the fuel gas results in combustion products, which include heat and any other gases or vapors which may result from the combustion of the fuel gas. The combustion products mix with the unburned portion of the air bag inflation gas 32. This produces an inflation fluid in the chamber 30 comprising the inert gas, the combustion products and any remaining fuel and/or oxidizer gas. The pressure in the chamber 30 rises due to warming of the inflation fluid by the heat produced by the combustion of the fuel gas.

When a predetermined pressure is reached in the chamber 30, the pressure of the inflation fluid in the chamber causes the inflation fluid to flow into the air bag 4. For example, a burst disk (not shown) may rupture to allow inflation fluid to flow into the air bag 4. As the inflation fluid flows into the air bag 4, the inflation fluid inflates the air bag 4 into a predetermined position (i.e., between the vehicle occupant and the instrument panel 7) to help protect the vehicle occupant from forcibly striking parts of the vehicle.

In accordance with the present invention, a cylindrical surface 36 extends between the first circular wall surface 26 and the second circular wall surface 28 of the first end cap 22. The cylindrical surface 36 defines a recess 38 in the first end cap 22. A cold gas species detector 50 is disposed in the recess 38. The detector 50 has a first end 52 exposed to the chamber 30 and a second end 54 presented away from the chamber 30. The first end 52 of the detector 50 contains a diode 60 (shown schematically in FIG. 2) which is exposed to, and in fluid communication with, the chamber 30. The diode 60 is thus exposed to, and in fluid communication and contact with, the air bag inflation gas 32 stored under pressure within the chamber 30.

A first pair of electrical conductors 64 extends between and connects the second end 54 of the detector 50 to a sensor or command module 70. The crash sensor could be included in the command module 70. A second pair of electrical conductors 72 extends between and connects the command module 70 with a warning indicator 74. The warning indicator 74 is preferably a light which is mounted on the instrument panel 7 in the vehicle compartment 8. The warning indicator 74 could also be an audible signal.

Figure 3:
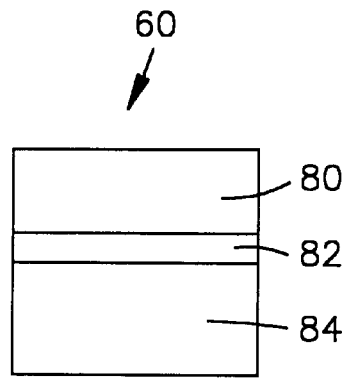
FIG. 3 is a schematic view of a part of FIG. 2.

The diode 60 is preferably a Schottky diode, and is preferably a Pd13% Ag Schottky diode, shown schematically in FIG. 3. The Pd13% Ag Schottky diode 60 comprises a catalyst metal film layer 80 of an alloy containing about 87% palladium and about 13% silver on a $SiO_2$ (silicon dioxide) layer 82. The $SiO_2$ layer 82 is adhered to an n-type Si (silicon) substrate 84.

An amount of hydrogen from the mixture of gases dissociates on the surface of the metal film layer 80 to form hydrogen ions. The hydrogen ions migrate to the interface between the metal film layer 80 and the oxide layer 82. The amount of hydrogen ions which migrate to the interface between the metal film layer 80 and the oxide layer 82 is proportional to the concentration of the hydrogen in the mixture of gases. A layer of hydrogen ions forms and causes a current, such as a forward current, of a first value across the diode 60 when a voltage is applied to the diode.

An input signal corresponding to the current of the first value is transmitted via the first pair of electrical conductors 64 to the command module 70. The command module 70 records and stores the first value.

If gas leaks from the chamber 30 of the inflator 10, the hydrogen gas will exit the chamber at a faster flow rate than the other gases in the mixture of gases (argon and oxygen). More particularly, the molecular weight of hydrogen is less than the molecular weight of the other gases, and the leak rate of a gas is directly proportional to the molecular weight of the gases.

As the concentration of hydrogen in the air bag inflation gas 32 in the chamber 30 drops, some of the hydrogen ions at the interface between the metal film layer 80 and the oxide layer 82 are released into the mixture of gases. This causes a decrease in the current across the diode 60.

As the current across the diode 60 drops, the input signal being sent to the command module 70 also drops. Once the command module 70 senses an input signal below a predetermined value relative to the first value, the command module sends an output signal via the second pair of electrical conductors 72 to the warning indicator 74 to illuminate the warning indicator. Illumination of the warning indicator 74 indicates to the vehicle occupant that the inflator 10 must be checked for a gas leak.

It should be appreciated that the command module 70 could send the output signal, via the second pair of electrical conductors 72, to a transmitter (not shown) for signaling a repair facility that the inflator 10 must be checked for a gas leak.

It should also be appreciated that since the concentration of the hydrogen in the mixture of gases is usually a predetermined value, the first value of the current across the diode 60 is also a predetermined value. The first value of the current thus can be programmed into the command module 70 instead of being determined by the diode 60 as described above.

It should also be further appreciated that the present invention is also applicable to inflators that conventionally do not contain any hydrogen, such as hybrid inflators. A hybrid inflator typically comprises a container housing a body of combustible material and a quantity of a stored gas. The body of combustible material is ignited and produces combustion products which heat and mix with the stored gas to form an inflation fluid for inflating the air bag 4. The stored gas in hybrid inflators typically consists of one or more inert gases, such as argon, nitrogen, helium, or a mixture thereof. In some hybrid inflators, the stored gas also comprises an oxidizer gas, such as oxygen, with the inert gas.

When using the detector 50 with a hybrid inflator, a quantity of hydrogen, preferably less than 4%, is stored with the other gas, or gases, and the hydrogen acts with the Schottky diode 60 as described above.

In another embodiment of the present invention, the air bag inflation gas 32 could contain a quantity of a detectable gas other than hydrogen, such as a hydrocarbon or a nitrogen oxide ($NO_x$). In this alternative embodiment, a diode whose current flows across itself is dependent upon the concentration of the hydrocarbon or the nitrogen oxide, respectively, would replace the Schottky diode 60 in FIG. 2. When the concentration of the hydrocarbon or the nitrogen oxide gas in the mixture of gases changes, the current across the diode would also change. The change in current across the diode is transmitted to the control module 70 via the first pair of electrical conductors 64. When the control module 70 receives a signal from the diode which indicates the current across the diode is at a predetermined level indicating a predetermined change in the concentration of the hydrocarbon or nitrogen oxide gas in the inflation gas 32, the command module transmits a signal which illuminates the warning indicator 74. The warning indicator 74 indicates to the vehicle operator that the inflator 10 is to be checked for gas leaks.

Figure 4:
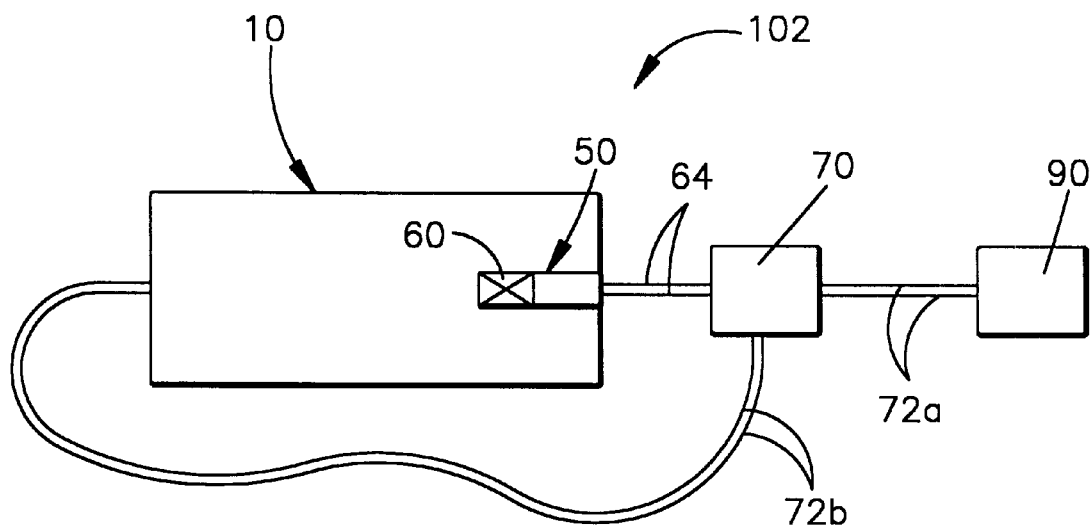
FIG. 4 is a schematic view of a vehicle occupant protection system which is constructed in accordance with a second embodiment of the present invention.

FIG. 4 illustrates a vehicle occupant protection system 102 constructed in accordance with a second embodiment of the present invention. The detector 50 housing the diode 60 is disposed in the inflator 10 and is connected to the command module 70 by the first pair of electrical conductors 64. The command module 70 is connected to a seat belt pretensioner 90 (shown schematically) by a second pair of electrical conductors 72a. The command module 70 is also connected to the igniter (not shown) of the inflator 10 by a third pair of electrical conductors 72b.

The diode 60 transmits input signals corresponding to the current flow across itself to the command module 70 via the first pair of electrical conductors 64 in the same manner as described above in the first embodiment. Once the command module 70 senses an input signal below a predetermined value, an output signal is sent to a part of the command module so that the command module is programmed to actuate the seat belt pretensioner 90 at an earlier time in the event of a collision. Also, the inflator could be actuated at an earlier time in the event of a collision. The earlier timing of actuation of the pretensioner and/or air bag could offset the loss of inflation fluid.

Thus, the command module 70 is part of a "smart restraint system" in which the perceived loss of inflation fluid is offset by firing a seat belt pretensioner or inflator earlier in the event of a collision.

From the above description of the invention, those skilled in the art will perceive improvements, changes and modifications. Such improvements, changes and modifications within the skill of the art are intended to be covered by the appended claims.

Having described the invention, the following is claimed:

1. Apparatus comprising:

an inflatable vehicle occupant restraint for, when inflated, helping to protect a vehicle occupant in the event of a collision;

an inflator having a housing defining a chamber;

a mixture of gases in said chamber for inflating said vehicle occupant restraint;

a diode supported by said housing and exposed to said stored mixture of gases in said chamber, an electrical property of said diode being dependent upon the concentration of at least one of said gases in said mixture of gases in said chamber;

sensor means for sensing the electrical property of said diode and providing an output signal when the electrical property of said diode reaches a predetermined threshold indicating a reduction in the concentration of at least one of said gases; and means responsive to said output signal for affecting vehicle occupant safety;

said means responsive to said output signal comprising means for controlling actuation of a seat belt pretensioner and said inflator.

2. Apparatus comprising:

an inflatable vehicle occupant restraint for, when inflated, helping to protect a vehicle occupant;

an inflator having a housing defining a chamber;

a mixture of gases stored in said chamber for inflating said vehicle occupant restraint;

a diode supported by said housing and exposed to said stored mixture of gases in said chamber, an electrical property of said diode being dependent upon the concentration of at least one of said gases in said mixture of gases in said chamber;

sensor means for sensing the electrical property of said diode, said sensor means providing an output signal when the electrical property of said diode reaches a predetermined threshold indicating a reduction in the concentration of said at least one of said gases; and means responsive to said output signal for affecting vehicle occupant safety;

said means responsive to said output signal comprising means for controlling actuation of a seat belt pretensioner and said inflator.

3. Apparatus comprising:

an inflatable vehicle occupant restraint for, when inflated, helping to protect a vehicle occupant in the event of a collision;

an inflator having a housing defining a chamber;

a mixture of gases stored under pressure in said chamber for inflating said vehicle occupant restraint wherein at least one of said gases is hydrogen;

a diode supported by said housing and exposed to said stored mixture of gases in said chamber, an electrical property of said diode being preferentially sensitive to the concentration of hydrogen in said chamber; and sensor means for sensing the electrical property of said diode and providing an output signal when the electrical property of said diode reaches a predetermined threshold indicating a reduction in the concentration of hydrogen in said chamber; and means responsive to said output signal for affecting vehicle occupant safety.

4. The apparatus as defined in claim 3 wherein said inflator has a recess in fluid communication with said housing, said diode being located in said recess, and said apparatus further including electrical conductors electrically connecting said diode and said sensor means.

5. The apparatus as defined in claim 3, wherein said diode is a Schottky diode.

6. The apparatus as defined in claim 5, wherein said diode comprises a metal alloy film layer comprising about 87% palladium and about 13% silver.

7. The apparatus as defined in claim 6 wherein said diode further comprises a silicon dioxide layer adjacent to said metal alloy film layer, and a silicon substrate adjacent to said silicon dioxide layer.

8. The apparatus as defined in claim 3 wherein said means responsive to said output signal is a warning indicator actuatable by said output signal.

9. The apparatus as defined in claim 8 wherein said warning indicator is mounted on an instrument panel of a vehicle.

* * * * *